US006582354B2

(12) United States Patent  (10) Patent No.: US 6,582,354 B2
Ellard  (45) Date of Patent: Jun. 24, 2003

(54) APPARATUS FOR LOADING RADIOACTIVE SEEDS AND SPACING ELEMENTS INTO A BRACHYTHERAPY NEEDLE

(75) Inventor: Terence R. Ellard, Seattle, WA (US)

(73) Assignee: Real World Design and Development Co., Seattle, WA (US)

( * ) Notice: Subject to any disclaimer, the term of this patent is extended or adjusted under 35 U.S.C. 154(b) by 0 days.

(21) Appl. No.: 09/911,899

(22) Filed: Jul. 23, 2001

(65) Prior Publication Data

US 2003/0018234 A1 Jan. 23, 2003

(51) Int. Cl.[7] .......................... A61M 36/00; A61N 5/00
(52) U.S. Cl. ......................................................... 600/8
(58) Field of Search .......................... 600/1–8; 222/168, 222/363; 141/2, 18, 21, 144, 145, 331, 344, 345

(56) References Cited

U.S. PATENT DOCUMENTS

| | | | | |
|---|---|---|---|---|
| 3,730,388 A | * | 5/1973 | Bender | 141/94 |
| 4,759,345 A | * | 7/1988 | Mistry | 250/507.1 |
| 5,906,574 A | * | 5/1999 | Kan | 221/211 |
| 6,113,529 A | * | 9/2000 | Shi | 600/1 |
| 6,358,195 B1 | * | 3/2002 | Green et al. | 600/7 |
| 6,402,677 B1 | * | 6/2002 | Jacobs | 600/7 |

* cited by examiner

Primary Examiner—Max F. Hindenburg
Assistant Examiner—Jonathan Foreman
(74) Attorney, Agent, or Firm—Jensen & Puntigam, P.S.

(57) ABSTRACT

The loading apparatus includes a tray assembly which receives radioactive seeds and spacer elements from containers thereof. The seeds and spacers move into a receiving portion of the apparatus. Guide wall assemblies are located between the wells in the tray assembly and a funnel opening which extends through the tray assembly at the front end thereof. Positioned beneath the funnel opening and removably attached to the tray assembly is a visualization and positioning assembly which has a vertical slot therein for receiving seeds and spacers. The seeds and spacers move by gravity through the funnel opening into the slot. A portion of the visualization assembly is transparent, permitting a visual inspection of the seed/spacer lineup in the slot. A control element at the lower end of the visualization assembly releases the seeds and spacers from the visualization member into a hollow needle located therebelow.

18 Claims, 3 Drawing Sheets

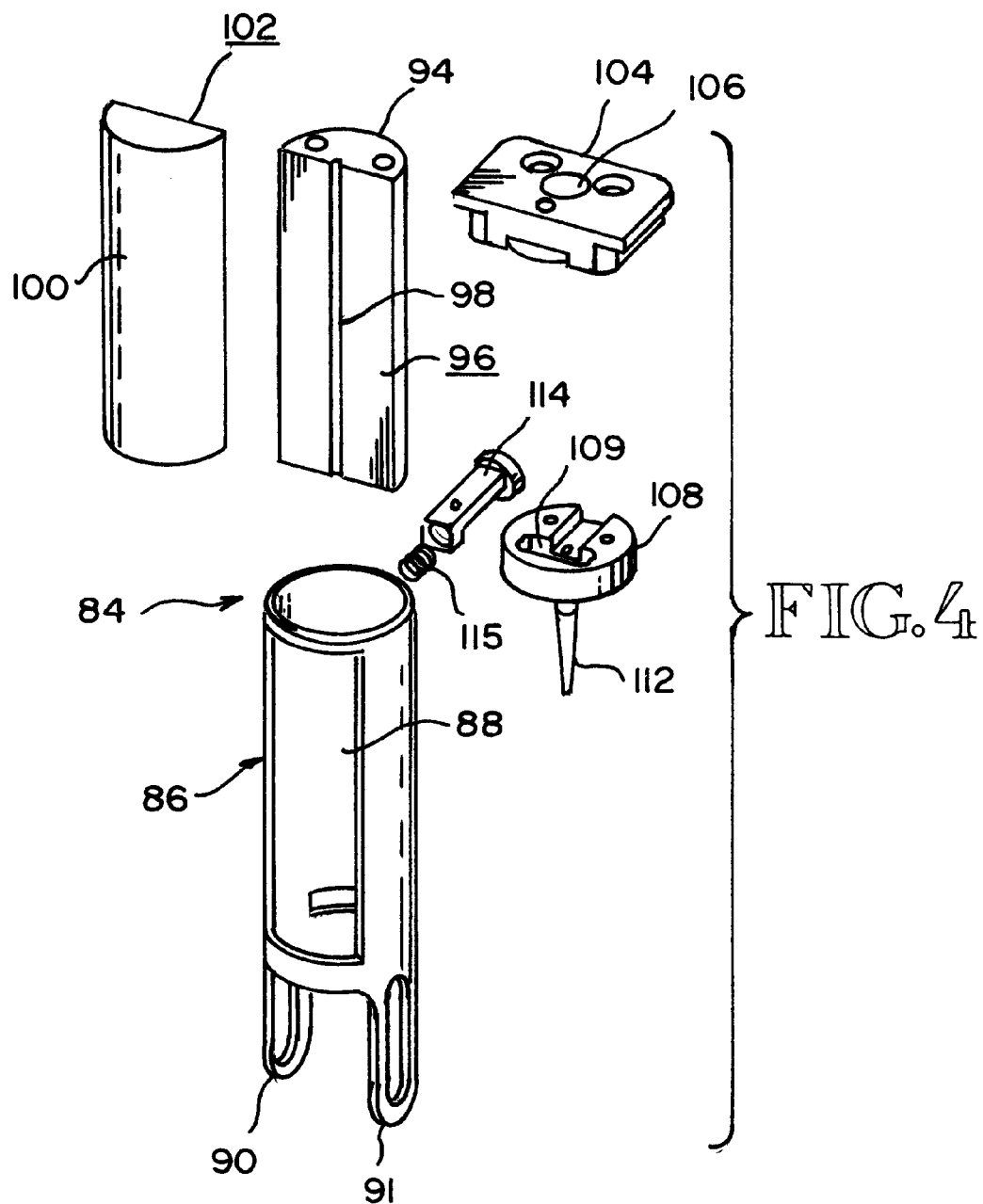

APPARATUS FOR LOADING RADIOACTIVE SEEDS AND SPACING ELEMENTS INTO A BRACHYTHERAPY NEEDLE

TECHNICAL FIELD

This invention relates generally to the filling of brachytherapy needles with radioactive seeds and spacers, and more specifically concerns an apparatus for loading and visually verifying radioactive seeds and spacers in a brachytherapy needle.

BACKGROUND OF THE INVENTION

Brachytherapy is a treatment regimen for prostate cancer involving the use of radioactive seeds/pellets and spacing elements (the spacing elements are not radioactive) in hollow, stainless steel needles. The loaded needles are inserted into the prostate in a preselected pattern specific to a given patient. The radioactive pellets are usually iodine No. 125 and/or palladium No. 103.

The brachytherapy technique in general is well known and is described in U.S. Pat. No. 5,871,448, which is hereby incorporated by reference, as well as numerous technical articles in various medical journals.

The needles are loaded individually with radioactive seeds and spacers, typically prior to insertion. Until recently, the radioactive seeds and spacing elements were loaded by hand, using tweezers specially adapted for handling the radioactive seeds. In this manual method, the technician/user grasps the seeds and the spacers alternately one by one with the tweezers and drops them (seed, spacer, seed, etc.) into the hollow needle. This manual loading is done behind a shield to protect the body and head of the user from exposure to the radiation from the seeds/pellets. The manual method has several disadvantages, including an inability to verify the correct loading of the needle, since the stainless steel needles are opaque. In addition, the hand and fingers of the user are still exposed to radiation. While considerable skill is necessary to perform the manual loading operation quickly, an expert operator can load as many as 25 needles in 10 minutes.

Devices have since been developed, however, which assist significantly in the loading of brachytherapy needles. In one case, tweezers are used to position radioactive seeds and spacers in a positioning tube mounted on a support member. The tube is transparent, which permits the arrangement of the seeds to be verified. The tube is then rotated on the support into alignment with a brachytherapy needle which is mounted at one side of the support and extends outwardly therefrom. The seeds and spacers are then moved horizontally by an insertion element into the needle. This device, however, is subject to jamming; the user is exposed to radiation from the seeds, and the extending needle creates a hazard. In addition, loading of brachytherapy needles with this device is time consuming.

In another development, the radioactive seeds and spacers are moved by a pusher tool from open wells in a tray to a horizontal groove in the tray, such that they are lined up in a desired order. The needle is positioned at one end of the groove, extending horizontally. The lined-up seeds and spacers in the groove can then be pushed into the needle by an insertion element. This device also has the disadvantage of exposure of the hands of the user to radiation and the chance of a needle stick. In a variation of this device, a lead acrylic shield is positioned over the tray, protecting the user fully from the radiation.

In still another development, the seeds and spacers are drawn into a positioning tube by a vacuum device and then moved from there into the brachytherapy needle. This device is somewhat cumbersome, however, and the complete sequence of actions to the completion of loading requires a substantial amount of time. The user's hands, moreover, are still exposed to radiation.

All of the above devices require more time than is desirable to load the needles. It is desirable to have a device by which a brachytherapy needle can be reliably and quickly loaded, with minimal or no exposure of the user to radiation, while permitting convenient visual inspection of the loaded seeds.

DISCLOSURE OF THE INVENTION

Accordingly, the present invention is an apparatus for loading radioactive seeds and spacers into a needle for use in the treatment of cancer in a localized portion of the body, comprising: a tray assembly which receives radioactive seeds and spacers, wherein the tray assembly includes a funnel portion into which the received seeds and spacers can be moved by use of a moving member, such as a small paddle; a visualizing and positioning assembly for said seeds and spacers located beneath the funnel portion of the tray assembly, the visualizing assembly including a vertically oriented slot into which the seeds and spacers fall by gravity after being moved into the funnel portion, the visualizing assembly being partially transparent to permit a user to verify the arrangement of seeds and spacers in the slot; and a control element in the visualizing and positioning assembly, permitting release of the seeds and spacers into a hollow needle.

BRIEF DESCRIPTION OF THE DRAWINGS

FIG. 4 is an exploded view of the visualization and alignment tube portion of the present invention.

BEST MODE FOR CARRYING OUT THE INVENTION

Figure 1:
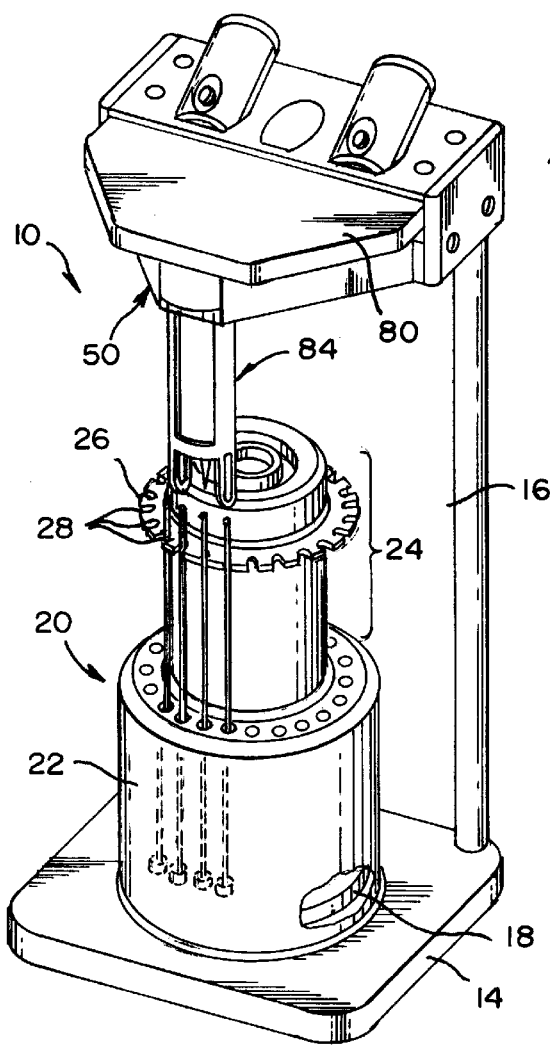
FIG. 1 is a perspective view of a complete loading system for brachytherapy needles.

FIG. 1 shows a complete brachytherapy needle loading mechanism incorporating the structure of the present invention. While the mechanism shown is particularly adapted for needles used in brachytherapy treatment of prostate cancer, it should be understood that the principles of the loading mechanism can be used for loading radioactive seeds and spacers into needles used for other cancer treatments and is not limited to loading brachytherapy-type needles.

The mechanism of FIG. 1 includes a loading stand which includes a small platform 14, which in the embodiment shown is approximately eight inches square with rounded corners and is approximately ¾ inch thick. Extending upwardly from the rear edge of the platform 14 are back support posts 16—16. In the embodiment shown, back support posts 16—16 are approximately 14 inches high with a diameter of approximately ⅝ inch. Both the back support posts 16—16 and the platform 14 are made of stainless steel.

In approximately the center of platform 14 is a circular raised mounting disc 18 upon which a needle holder 20 is positioned. Needle holder 20 can be easily rotated about mounting disc 18. Needle holder 20 is conventional in arrangement, with a lower cylindrical portion 22 and an upper cylindrical portion 24 which extends upwardly from lower cylindrical portion 22. Upper cylindrical portion 24 is smaller in diameter than the lower cylindrical portion 22. Near the upper surface of upper cylindrical portion 22 is an outwardly extending ring member 26 having individual radial slots 28—28 therein. Slots 28—28 are arranged to hold the upper portion of a brachytherapy needle in a vertical position. Ring member 26 has a selected number of slots 28—28, typically on the order of 24. Several needles 29—29 are shown; typically, there will be a ring of needles supported by the needle holder.

Figure 2:
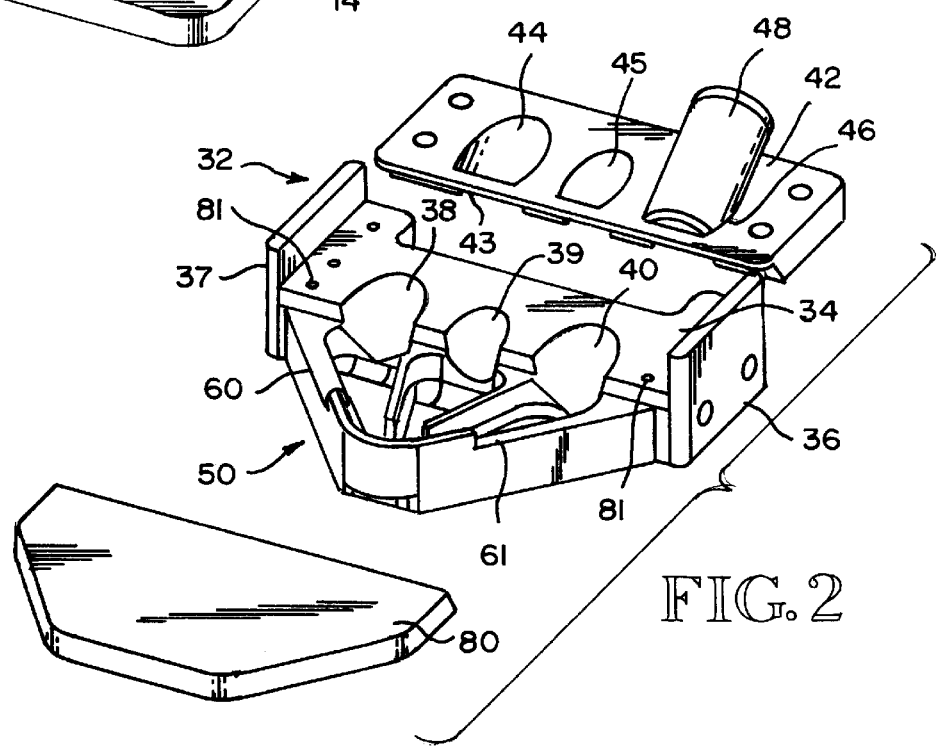
FIG. 2 is an exploded view of a loading tray portion of the present invention.
Figure 3A:
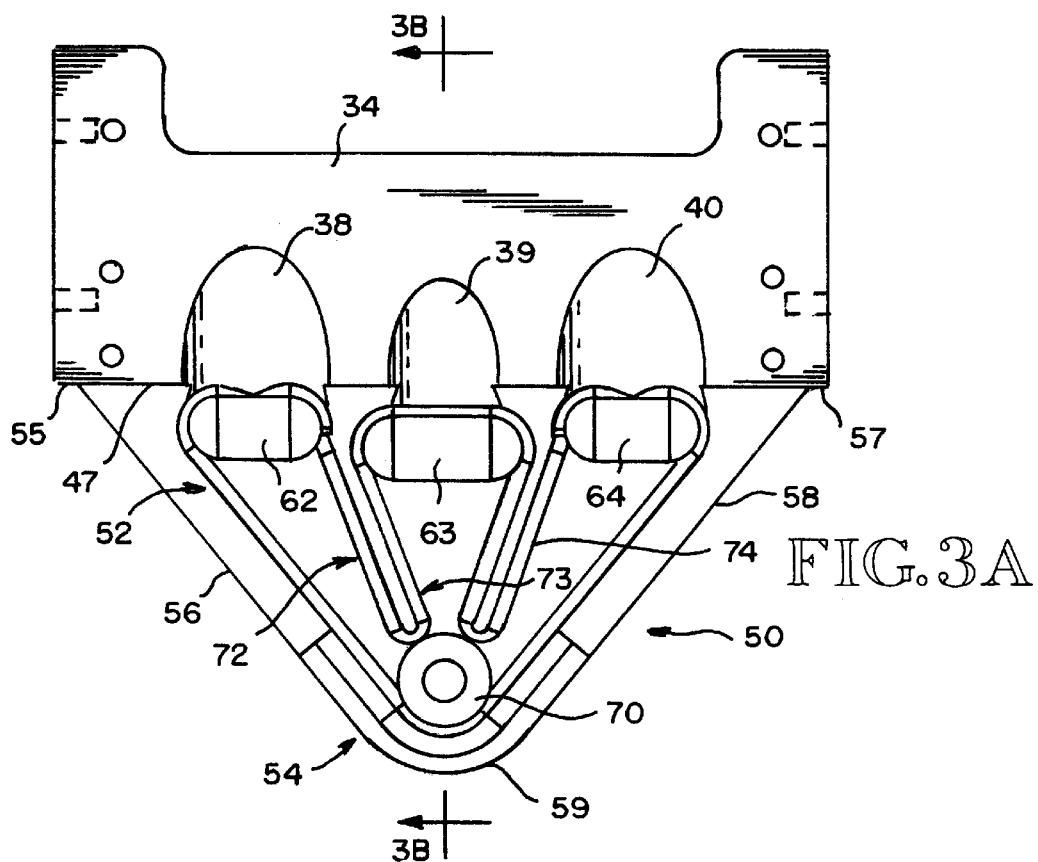
FIGS. 3A and 3B are top and cross-sectional views, respectively, of a part of the loading tray portion of the present invention.
Figure 3B:
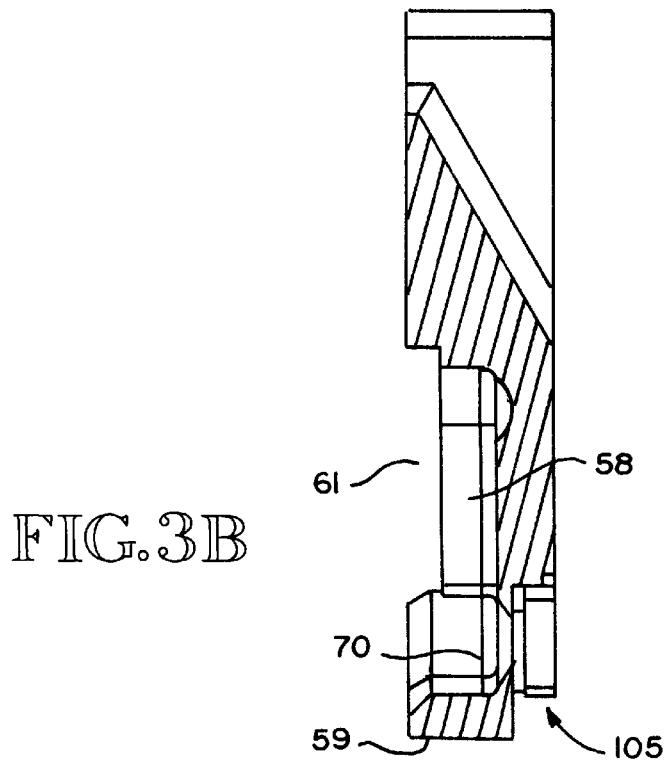

Extending horizontally from the upper end of rear support posts 16—16 is a radiation seed and spacer tray assembly 30, also referred to as a loading tray and/or a loading tray assembly. FIGS. 2 and 3 show the tray assembly 30 in detail. Tray assembly 30 includes a horizontal, rectangular plate portion 34 and two approximately square upright side portions 36, 37 secured to each end of horizontal plate portion 34. Along the front of horizontal plate 34 are three angled (sloped) scoop-like portions 38, 39 and 40. Scoop portions 38–40 extend from approximately the lateral mid-point of the horizontal plate 34 to forward edge 47 of the horizontal plate. Positioned between the top edges of the two side portions 36 and against the upper surface of plate 34 is a horizontal positioning plate 42. Plate 42 is the same length as plate 34 and the same width as plates 36, 37. The front edge of plate 42 includes a small forward lip 43. Three slanted openings 44, 45 and 46 are provided in positioning plate 42. Openings 44–46 are slanted so as to hold a seed or spacer container or to permit seeds/spacers to move down into the tray if positioned directly on the plate surfaces defining the openings. A representative container 48 is shown in FIG. 2.

Seed/spacer container 48 can take various configurations. In the embodiment shown, it is cylindrical. The openings 44–46 and cutout portions 38–40 in plate 34 are arranged to hold the container 48 at a specified angle relative to the two plates 34 and 42. In the embodiment shown, the angle is 30°, although it can be varied, depending upon the configuration of the container and other system variables. Other cross-sectional configurations for container 48 could be square, rectangular and still others. Also, it should be understood that a seed and/or spacer container is not necessary to the loading assembly of the present invention. The seeds/spacers can be provided in other ways, including by hand.

Three openings are provided in plate 42 to permit the possibility of having two separate loading paths for radioactive seeds with one path for spacers. However, other configurations are possible. One loading channel can be used for radioactive seeds and one for spacers, while the remaining one (of three) can be used for seeds and spacers which are returned to the loading tray from a misloaded needle. Only two loading channels, one for seeds and one for spacers, are necessary, however.

Extending forwardly from and positioned slightly below horizontal plate 34 is a triangular-shaped seed/spacer directing portion 50. Directing portion 50 includes a base section 52 bounded by an angled wall 54 which extends approximately from one end 55 of positioning plate 34 to the other end 57 thereof. Wall 54 includes two straight portions 56 and 58 which angle toward each other and a small center curved portion 59 which joins the two straight portions. Center portion 59 is approximately 3½ inches from the front edge 47 of horizontal plate 34 in the embodiment shown. The upper edge of wall 54 includes two cutout portions 60, 61, each of which are approximately three inches long, and extend, respectively, from the front edge of horizontal plate 34 a substantial part of each straight portion 56 and 58. The cutout portions are each approximately 5/16 inch high.

Located in base section 52 of directing portion 50 are three shallow wells 62, 63 and 64 for holding radioactive seeds and spacers. Each shallow well is approximately oval-shaped and located just below and slightly forwardly of cutout portions 38, 39 and 40 in horizontal plate 34. Hence, seeds or spacers move along the angled cutout portions and drop down into the three corresponding wells 62, 63 and 64. At the apex of base section 52, adjacent curved portion 59 of wall 54, is a funnel-like opening 70, which extends through the base section 52. In the embodiment shown, funnel opening 70 at the surface of base section 52 is approximately ⅞ inch in diameter, with the remainder of the opening through the base section being approximately ⅜ inch in diameter. These dimensions, however, can be varied.

Connecting each well 62–64 with funnel opening 70 are guide wall assemblies 72, 73 and 74 which, respectively, surround the rear of each well and extend from each well to the funnel opening 70. Each guide wall assembly narrows from the dimension of its associated well which, in the embodiment shown, is approximately 1¼ inches, to ⅜ inch, where it connects with the funnel opening 70. Each guide wall assembly is approximately ½ inch high and comprises a rear section which surrounds the rear and end edges of its associated well and forward portions which extend from each end of the well to the funnel-like opening 70. The guide wall assemblies 73, 74 and 75 act as a guide for movement of spacers and seeds from the wells into the funnel-like opening.

A flat protective shield 80 is positioned over the top of the triangular directing portion 50. Shield 80 is made from a radioactive-protective material, such as lead acrylic. Shield 80 is transparent so that the seed/spacer wells and guide wall assemblies and the individual radioactive seeds and spacer elements in the wells can be clearly seen through the shield. The peripheral edge of the shield extends beyond the peripheral edge of the directing portion by about ¾ inch. Shield 80 fits on top of the curved center portion 59 of wall 54, leaving the cutout portions 60 and 61 open. These open cutout portions permit the insertion of a paddle tool which can be used to move seeds and spacers from the wells 62–64 to the funnel opening 70. The guide wall assemblies and the flat shield 80 are positioned and configured to prevent radiation from the seeds from escaping through the open cutout portions.

The rear edge of shield 80 is held in place by the front lip 43 of plate 42 and by spring balls 81 in the upper surface of plate 34 located near the front edge thereof. The rear edge 83 of shield 80 is angled at and mates with the front edge (beneath lip 43) of plate 42.

The guide wall assemblies guide the radioactive seeds and the spacers into the funnel opening 70 after they have been pushed in that direction by the tool handled by the user. The guide wall assemblies are sufficiently low as to permit the use of the tool over the top edges thereof, i.e. they are approximately the same height as the height of the cutout portions in the wall 54. This arrangement protects the user's hands from radiation, as he/she uses the tool to push the radioactive seeds/spacer elements. The seeds, upon reaching funnel opening 70, move by gravity down through the funnel opening and the base portion 52 into a visualization and seed positioning assembly 84.

Visualization assembly 84 is shown in more detail in FIG. 4. It is positioned at and removable from the front-most portion of the directing portion 50 and receives seeds and spacers which move down through funnel opening 70. Visualization assembly 84 includes a cylindrical housing member 86. Housing member 86 includes an open front portion 88 which extends for substantially the length of housing 86 and extends around a substantial portion of the arcuate surface of the housing, approximately 120° in the embodiment shown. At the lower end of the housing 86 are two elongated extensions 90 and 91, which protect a downwardly extending valve portion, discussed below.

Positioned interiorly of housing 86 is a semicylindrical seed block 94 which is approximately the same length as housing 86. Extending lengthwise of the seed block 94 in a flat surface portion 96 of the seed block is a seed groove 98, which is large enough to accommodate the radioactive seeds and spacer elements which move into the assembly 84 from directing portion 50. Also positioned in housing 86 is a semi-cylindrical glass block 100, which mates with seed block 94 to form a solid cylinder with seed groove 98 extending down the center thereof. Glass block 100 has a flat surface 102 which comes directly adjacent flat surface 96 of seed block 94 within housing 86. Glass block 100 is transparent and made of lead acrylic in the embodiment shown.

Positioned at the top of housing 86 is a receiving element 104 which is configured to be inserted into and removed from, in a sliding ear/groove type arrangement, a mating portion 105 (FIG. 3B) in the lower surface of directing portion 50 at the front end thereof, beneath funnel opening 70. Receiving element 104 includes an opening 106 which is in registry with groove 98 in seed block 94, and also in registry with funnel opening 70 when the visualization assembly 84 is operatively positioned relative to directing portion 50. Receiving element 104 is connected to seed block 94 by screws or the like.

At the lower end of housing 86, directly beneath seed block 94 and glass block 100, is a valve element 108. Valve element 108 includes a disc-like portion having an opening 109 therethrough which connects to a descending loading spout 112. Movably positioned in the body of valve element 108 is an elongated valve shuttle element 114 (and spring 115) which is movable by an operator so that in one position, the opening 109 through valve 108 is blocked (the valve element is closed), while in another position, the opening 109 is clear so that the valve element is open, permitting seeds and spacers in slot 98 to fall therethrough.

In this arrangement, the seeds and spacers present in groove 98, which are visible to the user through the glass block 100, are ordinarily blocked from downward movement by shuttle 114. When the shuttle 114 is opened, however, the seeds and spacers are free to move downwardly through the valve element 108 through loading spout 112 into a vertically oriented needle located directly thereberneath. In FIG. 1, the needle is held by a particular needle holder 20, although holder 20 is not a necessary part of the present invention.

Also, when the visualization assembly 84 is loaded with seeds and spacers, it can be removed from the directing portion 50 and moved to a remote needle holder assembly for loading of seeds into a needle (if a needle holder is not located with the loading tray/visualization assembly) or it can be joined to a needle which has been inserted into a patient. An insertion element is then used to push the seeds/spacers into the needle.

In operation, seeds and spacers are initially loaded into the loading mechanism through openings 44, 45 and 46 in the positioning plate 42. They then move down along angled cutout portions 38, 39 and 40 in horizontal plate 34. The seeds and spacers move by gravity action along the angled cutout portion surfaces into the three wells 62, 63 and 64 in directing portion 50. The needle holder 20, with a plurality of needles held around the periphery thereof, has been previously operated to bring a particular needle to be filled directly beneath the loading spout 112 of the visualization assembly 84.

The user extends an elongated paddle element through open cutout portions (60, 61) between wall 54 and shield 80, moves the seeds and spacers by the paddle element one by one out of their respective wells and pushes them toward funnel opening 70. At the funnel opening, the seeds/spacers move by gravity action through the funnel opening into the visualization assembly 84. In particular, the seeds/spacers move into groove 98, which is in registry with funnel opening 70. When the desired combination of seeds and spacers has been loaded into the visualization assembly, and the correct arrangement (the desired one-by-one lineup of preselected seeds and spacers) has been verified visually by the user through glass block 100, shuttle element 109 is operated, permitting the seeds and spacers to fall by gravity into the needle. This process is repeated until all of the needles for a particular patient have been loaded, at which point the needle holder can be readily removed for use by the physician performing the brachytherapy technique. Alternatively, as explained above, the assembly 84 may be moved and connected to a pre-inserted needle where the seeds/spacers are loaded with an insertion tool.

The above-described apparatus has several advantages, including ease of operation, having a capability of fast, reliable loading of the brachytherapy needles. The seeds and spacers move by gravity within the apparatus and the needle to be loaded is positioned vertically, thereby eliminating the risk of needle sticks from horizontally positioned needles. In addition, the apparatus is arranged such that the user is protected from radiation by shielding, even the user's hands. Hence, the apparatus is safe to use as well as convenient. The visualization assembly 84, as indicated above, is removable from the directing assembly. The visualization assembly further is easily disassembled for cleaning and sterilization. Hence, the loading system of the present invention has substantial operating advantages relative to existing systems.

Although a preferred embodiment of the invention has been disclosed here for purposes of illustration, it should be understood that various changes, modifications and substitutions may be incorporated without departing from the spirit of the invention, which is defined by the claims which follow.

What is claimed is:

1. An apparatus for loading radioactive seeds and spacers into a needle for use in the treatment of cancer in a localized portion of the body, comprising:

a tray assembly for receiving radioactive seeds and spacers, the tray assembly including a funnel portion into which the received seeds and spacers can be moved by use of a moving member;

a visualizing and positioning assembly for said seeds and spacers located beneath the funnel portion of the tray assembly, the visualizing assembly including a vertically oriented slot into which the seeds and spacers fall by gravity after being moved into the funnel portion, the visualizing assembly being partially transparent to permit a user to verify the arrangement of seeds and spacers in the slot; and a control element in the visualizing and positioning assembly, permitting release of the seeds and spacers into a hollow positioned vertically below the visualizing assembly to receive seeds and spacers therefrom which move by gravity into the needle when released from the visualizing assembly.

2. An apparatus of claim 1, including a support for positioning the tray assembly and the visualizing assembly such that a needle to be filled can be located vertically therebeneath.

3. An apparatus of claim 2, wherein the tray assembly includes at least two wells for receiving seed and spacer elements, respectively, and wherein the tray assembly further includes guiding elements which extend between each well and the funnel portion for guiding the seeds and spacers to the funnel portion.

4. An apparatus of claim 3, wherein the tray assembly includes openings for holding containers of seeds and spacers, and wherein the tray assembly is configured such that seeds and spacers which are moved out of the containers move down into the wells by gravity action.

5. An apparatus of claim 3, including at least three wells and three guide elements, one of which is used to receive seeds and spacers from an incorrectly filled needle.

6. An apparatus of claim 3, including a radiation-protective shield positioned over the wells, the guide elements and the funnel portion, wherein the combination of the tray assembly and the shield is configured to define an opening which permits insertion of a tool to move the radioactive seeds and spacers from the wells into the funnel opening.

7. An apparatus of claim 1, wherein the visualizing assembly is attached to and removable from the tray assembly.

8. An apparatus of claim 1, wherein the visualizing assembly includes a transparent radiation-protective portion, permitting the user to verify the arrangement of the seeds and spacers therein.

9. An apparatus of claim 1, wherein the visualizing assembly includes a spout at a bottom portion thereof which extends operatively into the top of a needle positioned therebelow, wherein the control element releases the seeds and spacers through the spout.

10. An apparatus of claim 1, including a carrier assembly for holding needles to be loaded, the carrier being movable in such a manner that successive needles are positioned beneath the visualization assembly for loading of seeds and spacers therefrom.

11. An apparatus for loading radioactive seeds and spacers into a needle for use in the treatment of cancer in a localized portion of the body, comprising:

a tray assembly for receiving radioactive seeds and spacers, the tray assembly including a funnel portion into which the received seeds and spacers can be moved by use of a moving member, wherein the tray assembly includes at least two wells for receiving seed and spacer elements, respectively, and wherein the tray assembly further includes guiding elements which extend between each wall and the funnel portion for guiding the seeds and spacers to the funnel portion;

a visualizing and positioning assembly for said seeds and spacers located beneath the funnel portion of the tray assembly, the visualizing assembly including a vertically oriented slot into which the seeds and spacers fall by gravity after being moved into the funnel portion, the visualizing assembly being partially transparent to permit a user to verify the arrangement of seeds and spacers in the slot; and a control element in the visualizing and positioning assembly, permitting release of the seeds and spacers into a hollow needle.

12. An apparatus of claim 11, including a support for positioning the tray assembly and the visualizing assembly such that a needle to be filled can be located vertically therebeneath.

13. An apparatus of claim 11, wherein the tray assembly includes openings for holding containers of seeds and spacers, and wherein the tray assembly is configured such that when seeds and spacers which are moved out of the containers move down into the wells by gravity action.

14. An apparatus of claim 11, wherein the visualizing assembly includes a transparent radiation-protective portion, permitting the user to verify the arrangement of the seeds and spacers therein.

15. An apparatus for loading radioactive seeds and spacers into a needle for use in the treatment of cancer in a localized portion of the body, comprising:

a tray assembly for receiving radioactive seeds and spacers, the tray assembly including a funnel portion into which the received seeds and spacers can be moved by use of a moving member;

a visualizing and positioning assembly for said seeds and spacers located beneath the funnel portion of the assembly, the visualizing assembly including a vertically oriented slot into which the seeds and spacers fall by gravity after being moved into the funnel portion, the visualizing assembly being partially transparent to permit a user to verify the arrangement of seeds and spacers in the slot, wherein the visualizing assembly further includes a spout at a bottom portion thereof which extends operatively into a top of a needle positioned therebelow, wherein the control element releases the seeds and spacers through the spout.

16. An apparatus of claim 15, wherein the visualizing assembly includes a transparent radiation-protective portion, permitting the user to verify the arrangement of the seeds and spacers therein.

17. An apparatus for loading radioactive seeds and spacers into a needle for use in the treatment of cancer in a localized portion of the body, comprising:

a tray assembly for receiving radioactive seeds and spacers, the tray assembly including a funnel portion into which the received seeds and spacers can be moved by use of a moving member;

a visualizing and positioning assembly for said seeds and spacers located beneath the funnel portion of the tray assembly, the visualizing assembly including a vertically oriented slot into which the seeds and spacers fall by gravity after being moved into the funnel portion, the visualizing assembly being partially transparent to permit a user to verify the arrangement of seeds and spacers in the slot;

a control element in the visualizing and positioning assembly, permitting release of the seeds and spacers into a hollow needle; and a carrier assembly for holding needles to be loaded, the carrier being movable in such a manner that successive needles are positioned beneath the visualizing assembly for loading the seeds and spacers therefrom.

18. An apparatus for loading radioactive seeds and spacers into a needle for use in the treatment of cancer in a localized portion of the body, comprising:

a seed and spacer assembly for receiving radioactive seeds and spacers, the seed and spacer assembly including a guide portion into which the received seeds and spacers can be moved by use of a moving member;

a visualizing and positioning assembly for said seeds and spacers located beneath the guide portion of the seed and spacer assembly, the visualizing assembly including a single, vertically oriented slot into which the seeds and spacers fall by gravity after being moved into the guide portion, the visualizing assembly being partially transparent to permit a user to verify the arrangement of seeds and spacers in the slot; and a control element in the visualizing and positioning assembly, permitting release of the seeds and spacers downwardly by gravity action into a hollow needle.

* * * * *